US008992831B2

(12) United States Patent
Sumner et al.

(10) Patent No.: US 8,992,831 B2
(45) Date of Patent: Mar. 31, 2015

(54) STABILIZED CHLORINE DIOXIDE TO PRESERVE CARBOHYDRATE FEEDSTOCKS

(75) Inventors: Eric Guy Sumner, Hockessin, DE (US); Derrick Okull, Wilmington, DE (US); Ethan Baruch Solomon, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 129 days.

(21) Appl. No.: 12/889,979

(22) Filed: Sep. 24, 2010

(65) Prior Publication Data

US 2011/0236257 A1    Sep. 29, 2011

Related U.S. Application Data

(60) Provisional application No. 61/245,763, filed on Sep. 25, 2009.

(51) Int. Cl.
*A61L 2/18* (2006.01)
*A01N 59/00* (2006.01)
*A23L 3/358* (2006.01)
*C01B 11/02* (2006.01)

(52) U.S. Cl.
CPC ............... *A01N 59/00* (2013.01); *A23L 3/358* (2013.01); *C01B 11/024* (2013.01); *Y02E 50/16* (2013.01); *Y02E 50/17* (2013.01)
USPC .............................................. 422/37; 422/28

(58) Field of Classification Search
USPC ..................................................... 422/28, 37
See application file for complete search history.

(56) References Cited

U.S. PATENT DOCUMENTS

| | | |
|---|---|---|
| 2,546,568 A | 3/1951 | Taylor |
| 3,585,147 A | 6/1971 | Gordon |
| 3,591,515 A | 7/1971 | Lovely et al. |
| 4,040,977 A | 8/1977 | Eggensperger et al. |
| 4,689,215 A | 8/1987 | Ratcliff |
| 4,786,492 A | 11/1988 | Ratcliff |
| 4,788,053 A | 11/1988 | Ratcliff |
| 4,792,442 A | 12/1988 | Ratcliff |
| 4,793,989 A | 12/1988 | Ratcliff |
| 4,808,389 A | 2/1989 | Ratcliffe |
| 4,818,519 A | 4/1989 | Ratcliff |
| 4,837,009 A | 6/1989 | Ractliff |
| 4,886,657 A | 12/1989 | Ratcliff |
| 4,925,656 A | 5/1990 | Ratcliff |
| 4,929,365 A | 5/1990 | Clark et al. |
| 5,151,447 A | 9/1992 | Amick |
| 5,200,171 A | 4/1993 | Ratcliff |
| 5,252,343 A | 10/1993 | Kross |
| 5,348,734 A | 9/1994 | Ratcliff |
| 5,993,864 A | 11/1999 | Kross |
| 6,039,934 A | 3/2000 | Alliger |
| 6,284,152 B1 | 9/2001 | Kross |
| 6,306,281 B1 | 10/2001 | Kelley |
| 6,432,322 B1 | 8/2002 | Speronello et al. |
| 6,610,282 B1 | 8/2003 | Ghosh |
| 6,660,287 B1 | 12/2003 | Khanna et al. |
| 8,252,350 B1 * | 8/2012 | Cadwalader et al. ........... 426/14 |
| 2002/0117445 A1 | 8/2002 | Whiteman |
| 2003/0190742 A1 | 10/2003 | Whiteman |
| 2004/0237845 A1 | 12/2004 | Hunton |
| 2005/0272606 A1 | 12/2005 | Manchak, Jr. |
| 2006/0018940 A1 | 1/2006 | DiPietro et al. |
| 2006/0251762 A1 | 11/2006 | Jansen et al. |
| 2007/0034570 A1 | 2/2007 | DiMascio |
| 2008/0274206 A1 | 11/2008 | Lekhram et al. |
| 2009/0016973 A1 | 1/2009 | Ratcliff et al. |
| 2009/0054375 A1 | 2/2009 | Harrison et al. |
| 2009/0061490 A1 | 3/2009 | Edwards et al. |
| 2009/0087897 A1 | 4/2009 | Sumner et al. |
| 2009/0104157 A1 * | 4/2009 | Solomon et al. ............. 424/93.6 |
| 2010/0291649 A1 * | 11/2010 | Solomon et al. .............. 435/161 |

FOREIGN PATENT DOCUMENTS

| | | |
|---|---|---|
| CA | 965699 A1 | 4/1975 |
| CN | 1048200 A | 1/1991 |
| CN | 1122189 A | 5/1996 |
| CN | 1185417 A | 6/1998 |
| CN | 1415533 A | 5/2003 |
| CN | 1439268 A | 9/2003 |
| CN | 1454837 A | 11/2003 |
| CN | 1565193 A | 1/2005 |
| CN | 1582661 A | 2/2005 |
| CN | 1587029 A | 3/2005 |
| CN | 1596654 A | 3/2005 |
| CN | 1631769 A | 6/2005 |
| CN | 1631770 A | 6/2005 |

(Continued)

OTHER PUBLICATIONS

Agarwal, SKD, "Prevention of Rapid Deterioration of Sugarcane Molasses During Storage", Sugar Journal, 1987, vol. 47(7), 13-15.
Bischoff, Kenneth M. et al., "Modeling Bacterial Contamination of Fuel Ethanol Fermentation", Biotechnology and Bioengineering, 2009, vol. 103(1), 117-122.
Chen, Shaogang et al., "Experimental Observation on Germicidal Efficacy and Corrosiveness of Stable Chlorine Dioxide", Zhongguo Xiaoduxue Zazhi (2002), vol. 19(2), 107-110.
Fu, Daren et al., "Experimental Observation on Germicidal Efficacy of Stable Chlorine Dioxide Solution", Zhongguo Xiaoduxue Zazhi (2003), vol. 20(2), 95-98.

(Continued)

*Primary Examiner* — Sean E Conley

(57) ABSTRACT

A process to preserve a carbohydrate feedstock against contaminant microorganisms comprises contacting the carbohydrate feedstock with a stabilized chlorine dioxide at a pH of at least 2.6. The carbohydrate feedstock preferably comprises a naturally-occurring carbohydrate, particularly a carbohydrate having a reducing end group. The process is particularly suitable to treat feedstocks used in biorefining processes, such as in ethanol fermentation.

19 Claims, No Drawings

(56) References Cited

FOREIGN PATENT DOCUMENTS

| | | |
|---|---|---|
| CN | 1644488 A | 7/2005 |
| CN | 1759679 A | 4/2006 |
| CN | 1969633 A | 5/2007 |
| CN | 101011595 A | 8/2007 |
| CN | 101138364 A | 3/2008 |
| CN | 101138644 A | 3/2008 |
| CN | 101176446 A | 5/2008 |
| CN | 101176469 A | 5/2008 |
| CN | 101185443 A | 5/2008 |
| CN | 101187150 | 5/2008 |
| CN | 101249951 A | 8/2008 |
| CN | 101253881 A | 9/2008 |
| CN | 101253885 A | 9/2008 |
| CN | 101292667 A | 10/2008 |
| CN | 101356925 A | 2/2009 |
| CN | 101366392 A | 2/2009 |
| CN | 101380031 A | 3/2009 |
| EP | 0371728 B1 | 1/1997 |
| JP | 60054311 A | 3/1985 |
| JP | 60066973 A | 4/1985 |
| JP | 60067402 A | 4/1985 |
| JP | 60067403 A | 4/1985 |
| JP | 60068857 A | 4/1985 |
| JP | 60069005 A | 4/1985 |
| JP | 60075231 A | 4/1985 |
| JP | 60097910 A | 5/1985 |
| JP | 60101195 A | 6/1985 |
| JP | 60102134 A | 6/1985 |
| JP | 60114142 A | 6/1985 |
| JP | 60130336 A | 7/1985 |
| JP | 62170252 A | 7/1987 |
| JP | 63248896 A | 10/1988 |
| JP | 01099559 | 4/1989 |
| JP | 04046003 | 2/1992 |
| JP | 2000154003 A | 6/2000 |
| JP | 2000202010 A | 7/2000 |
| JP | 2000211901 A | 8/2000 |
| JP | 2005211644 A | 8/2005 |
| JP | 3882939 B1 | 2/2007 |
| KR | 9303658 B | 5/1993 |
| WO | 8903179 A1 | 4/1989 |
| WO | 0135746 A1 | 5/2001 |
| WO | 2005000368 A1 | 1/2005 |
| WO | 2006014720 A1 | 2/2006 |
| WO | 2006038802 A1 | 4/2006 |
| WO | 2007097874 A1 | 8/2007 |
| WO | 2007149450 A2 | 12/2007 |
| WO | 2008111357 A1 | 9/2008 |
| WO | 2008111358 A1 | 9/2008 |
| WO | 2009009163 A1 | 1/2009 |

OTHER PUBLICATIONS

He Qihuan et al., "Study on Organic Stabilized Chlorine Dioxide", Gongye Shuichuli (2004), vol. 24(2), 49-52.

International Search Report, US Commissioner for Patents, Alexandria, Virginia, in PCT/US2010/050342, PCT Counterpart of U.S. Appl. No. 12/889,979.

Jacques, K.A. et al., "The Alcohol Textbook", Nottingham University Press, UK, 4$^{th}$ Edition, 2003, 424-426.

Kaczur, Jerry J. et al., "Chlorine Oxygen Acids and Salts, Chlorous Acid, Chlorites, and Chlorine Dioxide", Kirk-Othmer Encyclopedia of Chemical Technology, Published Online Dec. 4, 2000, 1-26.

Kwiatkowski, Jason R. et al., "Modeling the Process and Costs of Fuel Ethanol Production by the Corn Dry-Grind Process", Industrial Crop and Products 23 (2006), 288-296.

Liu, Li et al., "Use of Stabilized Chlorine Dioxide as Bactericide at Pingqiao Water Treating Plant", Youtian Huaxue (2006), vol. 23(1), 42-45, 58.

Rendleman, C. Matthew et al., "New Technologies in Ethanol Production", U.S.D.A. Agricultural Economic Report Feb. 2007, No. 842.

Schell, Daniel J. et al., "Contaminant Occurrence, Identification and Control in a Pilot-Scale Corn Fiber to Ethanol Conversion Process", Bioresource Technology 98 (2007) 2942-2948.

Sun, Xianfeng et al., "Experimental Observation on Efficacy of Chlorine Dioxide and Sodium Hypochlorite in Disinfection of Garlic Clove", Zhongguo Xiaoduxue Zazhi (2005), Vol. 22(4), 406-407.

Yin Changchun et al., "Preparation of Stable Chlorine Dioxide and Research on Its Stability", Huaxue Gongye Yu Gongcheng (Tianjin) (1999), Vol. 16(3), 181-183.

Yu, Li et al., "Study on Preparation and Application of Stable Solid Chrlorine Dioxide", Henan Huagong (2006), vol. 23(8), 23-24.

\* cited by examiner

STABILIZED CHLORINE DIOXIDE TO PRESERVE CARBOHYDRATE FEEDSTOCKS

FIELD OF THE INVENTION

The present invention relates a process for substantially preventing microbial growth, in a carbohydrate feedstock, during storage or transport including a process wherein the solution or suspension is a feedstock intended for fuel ethanol production.

BACKGROUND OF THE INVENTION

Recently there has been substantial growth in integrated biorefineries in which any number of agricultural feedstocks can be converted into renewable fuels as well as higher-value chemicals, materials, and pharmaceuticals. A biorefinery operates on a concept similar to a petrochemical refinery. Incoming feedstocks for biorefineries include traditional agricultural products such as corn, milo, wheat, barley, millet, straw, sorghum, sugar cane, sugar beets, molasses, whey, fruits, and potatoes, and also other products that are currently classified as waste streams such as wood waste, bagasse, paper waste, and municipal solid waste. An appeal of such feedstocks is the carbohydrate content, which can be exploited as a reactant in a biorefinery. The products from a biorefinery may be intended for human consumption, such as sugar produced from sugar cane or molasses produced from sugar beets or for use as fuel or in chemical synthesis, such as ethanol and succinic acid produced from corn.

A particular application of biorefining is the production of fuel ethanol. As petroleum reserves become depleted and more expensive, the need for alternative, and preferably sustainable, energy sources increases. Ethanol is an option for partial or complete replacement of petroleum-based fuels for different applications. Ethanol-powered automobiles are a reality. Ethanol has advantages over the use of conventional gasoline as a renewable fuel source.

Currently both industrial ethanol (e.g., fuel) and beverage ethanol are produced on large scale from agricultural (natural) feedstocks by fermentation processes in which sugar is converted to ethanol and carbon dioxide by inoculant yeast. Many feedstocks can be used to provide the sugar for fermenting, including potentially, any starch or cellulosic material, which includes nearly all plants, as any starch or cellulose can be a precursor to sugar. Some of the common feedstocks particularly suitable for producing fuel ethanol include corn, milo, sorghum, sugar cane, sugar beets and molasses.

A significant problem facing biorefineries is spoilage of feedstocks during storage and transport. As raw agricultural materials, these feedstocks typically contain high levels of undesirable microorganisms such as bacteria, fungi, and undesirable yeasts that can degrade (spoil) the feedstock prior to entering a biorefining process. These microorganisms may be introduced as part of the original source of the feedstock or from preliminary preparation steps for corn feedstocks. Undesirable microorganisms may contain enzymes which convert the feedstocks into sugars that are metabolized by the microorganism facilitating its growth. Thus, valuable feedstock is lost as it is consumed by the microorganism. Growth of these microorganisms reduces the value of the incoming feedstock. In a particular example, a significant problem with the storage of molasses and sugar cane or sugar beet juice is deterioration of the sugar content due to the action of spoilage microorganisms such as *Leuconostoc* or *Lactobacillus*.

While biocides are generally suitable to treat materials containing undesirable microorganisms, they are non-specific and attack target and non-target microorganisms. Biocides perform poorly in fermentation systems, because they can attack the inoculant yeast. Chlorine dioxide is a biocide that has been used in fermentation systems to treat microorganism infection. The chlorine dioxide may be introduced as chlorine dioxide gas from a suitable chlorine dioxide generator. Alternatively, stabilized chlorine dioxide (SCD) can be activated by contact with acid. Use of SCD to prevent microorganism infection in the presence of acid is disclosed in WO 2007/149450.

Ziegler discloses in WO 2007/097874 a method to reduce undesirable microorganisms, such as bacteria, contaminant yeast or killer yeast, in a fermentation process using chlorine dioxide ($ClO_2$) gas. This process requires generation equipment and reactants necessary to generate $ClO_2$ gas. The generated $ClO_2$ must be used as it is produced, because it degrades when exposed to light, or when in contact with any organic matter such as would be present in a fermentation process. Ziegler teaches against use of stabilized chlorine dioxide as being difficult and imprecise, with potential to kill desire yeast and/or inhibit needed enzymes.

Stabilized chlorine dioxide is available commercially. Stabilized chlorine dioxide is generally a buffered solution (e.g., using a carbonate buffer for alkaline pH) of sodium chlorite, although other sources of chlorine dioxide also exist. Buffered sodium chlorite solutions are stable for long periods of time. Buffered sodium chlorite solutions can generate chlorine dioxide when activated, such as by chemical oxidation (e.g., with ozone or chlorine), electrochemical oxidation, or acidification (e.g., using a strong acid such as HCl). See, e.g., "Chlorine Oxygen Acids and Salts, Chlorous Acid, Chlorites and Chlorine Dioxide" by Jerry J. Kaczur and David W. Cawlfield, published online: 4 Dec., 2000, in Kirk-Othmer Encyclopedia of Chemical Technology.

There remains a need for a process to reduce the level of microorganism contaminants in feedstocks intended for use in a range of biorefinery processes. Carbohydrate-containing feedstocks, including sugar crops and cellulose feedstocks, are susceptible to spoilage from microorganisms. Biorefinery processes include manufacture of fuel ethanol, breakdown of cellulose containing biomass, sugar production (from sugar cane and/or sugar beets), sugar cane refining, processing of starches, such as potato starch and corn starch, among others. There is a further need for a process to prevent deterioration of feedstocks, such as carbohydrate solutions and suspensions, during storage and transportation.

It is desired to have a simple and economical process to stabilize carbohydrate feedstocks in storage and in transport. It is desired to have a process which does not introduce unnecessary and/or undesirable agents into the feedstock, particularly agents which adversely affect the quality of biorefinery products, such as ethanol.

The present invention meets these needs.

SUMMARY OF THE INVENTION

A process to preserve a carbohydrate feedstock against contaminant microorganisms comprises or consists essentially of or consists of contacting the carbohydrate feedstock with a stabilized chlorine dioxide at a pH of at least 2.6. The concentration of the carbohydrate in the feedstock is at least 1% and preferably ranges from 1 to 70%, by weight, based on the total feedstock weight. The amount of stabilized chlorine dioxide is 10 to 10000 mg/kg, as available chlorine dioxide, based on the total feedstock weight. The carbohydrate feedstock preferably comprises a naturally-occurring carbohydrate. Surprisingly, the process is effective in the absence of added acid or oxidant to generate chlorine dioxide.

DETAILED DESCRIPTION

Trademarks herein are denoted in upper case.

The present invention comprises a process to preserve a carbohydrate feedstock against deterioration by contaminant microorganisms. The carbohydrate feedstock may be a carbohydrate solution or suspension in an aqueous medium. By the term "aqueous medium" as used herein is meant the medium is substantially water, such as for example greater than 80% water, preferably greater than 90% water, more preferably greater than 95% water. The aqueous medium can be greater than 99% water.

The process comprises or consists essentially of or consists of contacting the carbohydrate solution or suspension with a stabilized chlorine dioxide at a pH of at least 2.6, preferably at least 3, preferably at least pH 3.5, preferably at least pH 4, preferably at least pH 4.5 and preferably not greater than pH 9. The concentration of the carbohydrate is at least 1% in the feedstock, preferably 1 to 70%, based on the total feedstock weight, and the amount of stabilized chlorine dioxide added is 10 to 10000 mg/kg as available chlorine dioxide content, based on the total feedstock weight.

Preservation

By the terms "preserve" and "preservation" as applied herein to a carbohydrate feedstock is meant prevention of reaction or consumption of carbohydrate by contaminant microorganisms such as bacteria. Preservation provides a stable carbohydrate feedstock that does not undergo substantial change, such as would result from reaction or consumption due to microbiological metabolism, over a period of time of at least one month. One measure of change is the microbial population of the preserved feedstock. When properly preserved, the carbohydrate feedstock does not undergo an increase in the microbial population in the feedstock of more than 1 $\log_{10}$ CFU/ml or 1 $\log_{10}$ CFU/g. Typically microbial population is expressed as log 10 CFU/ml for liquid feedstocks and as log 10 CFU/g for solid/semi-solid feedstocks. The expression log 10 CFU/g can also be used for liquid feedstocks.

A second measure of change is pH of the preserved feedstock should not change by more than 0.5 pH units. While pH measurement provides a more rapid assessment of preservation effect than measurement of microbial population, it will be appreciated by those skilled in the art that pH change may not be sufficient under all circumstances to monitor preservation of (i.e., lack of change in) a carbohydrate feedstock. For example, for buffered feedstocks or feedstocks at pH less than about pH 6, substantial microbial contamination may occur before pH changes by 0.5 pH units.

It will be further appreciated by those skilled in the art that other measures of change may be used. For example, detection of the presence of undesired compounds may indicate change, such as a product from metabolism of the carbohydrate feedstock. Detection methods may include spectrophotometry, chromatography, and other methods known to those skilled in the art. Still other measures may include physical changes to the carbohydrate feedstock such as specific gravity or viscosity.

The present invention relates to a method of preserving a carbohydrate feedstock in unit operations. By "unit operations" is meant any operation involving the carbohydrate feedstock, and in particular, storage, transport, pre-processing and production. "Pre-processing" means herein any step taken immediately prior to use of the feedstock. Pre-processing immediately prior to use of the feedstock include transfer of the feedstock from one vessel, e.g., storage, to a second vessel, e.g., fermentation tank, such as in a biorefinery for production of ethanol.

Production operations include processes for the production of a carbohydrate feedstock that is a non-fermented product, such as sugar. The preservation prevents or delays deterioration associated with microbial activity in the feedstocks. The feedstocks are used for subsequent conversion into end products via fermentation or similar processes, or incorporation into other processes used to produce end products.

Carbohydrate Feedstock

A "carbohydrate" as used herein is a monosaccharide, a disaccharide, an oligosaccharide, or a polysaccharide. Carbohydrates as used herein can be monosaccharides, disaccharides, oligosaccharides, polysaccharides, or mixtures of two or more thereof. Examples of monosaccharides, disaccharides, oligosaccharides, and polysaccharides are known to those skilled in the art. The carbohydrate is preferably a naturally-occurring carbohydrate. The naturally-occurring carbohydrate may or may not have a reducing end group. Such carbohydrates are more readily metabolized, and therefore more susceptible to deterioration by microorganisms.

Depending on the intended use, a carbohydrate feedstock comprising non-monosaccharide carbohydrates may require pretreatment such as hydrolysis to convert the non-monosaccharide carbohydrates to fermentable sugars. For example, a carbohydrate feedstock may consist of cornstarch in water. Cornstarch is a polysaccharide made up of individual units of glucose that are linked together. The cornstarch may be pretreated to convert the polysaccharide sequentially to smaller (shorter) polysaccharides (dextrins) and to glucose (a monosaccharide), for example, by using enzymes. The carbohydrate feedstock may also be in the form of a mash. The term "mash" as used herein is a composition comprising a fermentable sugar or a precursor to a fermentable sugar. More generally, mash includes any mixture of grain or other carbohydrate in water that is used in the production of ethanol. Mash can refer to carbohydrate-containing compositions used at any stage in ethanol fermentation, from mixing which occurs prior to cooking and/or saccharification of a fermentable sugar precursor to the composition produced upon completion of fermentation. Mash is further defined in Jacques, K. A., Lyons, T. P., Kelsall, D. R, "The Alcohol Textbook", 2003, 426-424, Nottingham University Press, UK.

A carbohydrate feedstock can be a solution or suspension of a fermentable sugar. More specifically, a fermentable sugar as used herein is a solution or suspension of a carbohydrate that is derived from essentially any plant source comprising sugar, starch and/or cellulose. That is, starch and/or cellulose can be converted by processes known in the art, e.g., using enzymes, to a fermentable sugar. The fermentable sugar can be derived from one or more of any grain-based product such as corn, wood chips, wheat straw, corn stover, switch grass. The fermentable sugar may alternatively be derived from milo, barley, millet, sorghum, sugar cane, sugar beets, molasses, whey, potatoes, algae, seaweed, and other biological sources. Processes are known to those skilled in the art to convert the plant sources to a fermentable sugar. Conveniently, the fermentable sugar is derived from corn, using either the wet mill or dry mill process to produce a liquefied starch. The liquefied starch undergoes saccharification, in which the starch is contacted with enzymes to convert the starch to glucose, thus forming the fermentable sugar.

The carbohydrate feedstock may comprise up to 100% by weight of carbohydrates. Generally the carbohydrate feedstock comprises between 1% and 70% carbohydrate based on the total weight of the feedstock, preferably between 2 and 40%. The amount and composition of the carbohydrates in the feedstock can vary depending on the intended end use. For example, corn steep liquor, which is a carbohydrate solution is obtained from a wet mill process, may comprise 16.5% carbohydrates. In a wet mill process, corn is soaked or steeped and then separated into various components. The corn steep liquor is the aqueous liquid obtained after the corn has been soaked for an extended period, during which readily fermentable soluble components are extracted from the corn solids into the steep water. The starch component from the wet mill process may comprise up to 40% by weight carbohydrates.

The carbohydrate feedstock may comprise other components generally functioning as adjuncts to the solutions and/or suspensions. For example, the carbohydrate feedstock may comprise enzymes, surfactants, dispersants, antifoaming compositions, minerals, trace elements, and combinations of two or more thereof. These components and other components that act as adjuncts are well-known to those skilled in the art. The carbohydrate feedstock may comprise up to 70% by weight, based on the total feedstock weight of the other components, preferably the carbohydrate feedstock comprises 2 to 40% by weight, more preferably, 2 to 35% by weight of one or more of the components.

Microorganisms

Microorganisms in the context of this invention are in two categories, desirable and undesirable microorganisms. Desirable microorganisms such as *Saccharomyces cerevisiae* are used in the fermentation of glucose into ethanol and carbon dioxide. Other desirable microorganisms are used in other biorefinery processes. Desirable microorganisms are not typically present in carbohydrate feedstocks.

Undesirable microorganisms include bacteria, fungi, wild or contaminant yeasts, and other microorganisms capable of metabolizing components of a carbohydrate feedstock to sustain the viability of the microorganism. Undesirable microorganisms contaminate carbohydrate feedstocks, utilize the feedstock as a food source, multiply, and thus deplete the feedstock.

Undesirable microorganisms such as contaminant yeasts are often found in both industrial and beverage ethanol production, and can cause severe episodes of contamination, resulting in reduced ethanol productivity.

These unwanted microorganisms are introduced into the process through the feedstock, process water, air, operators, and numerous other sources.

Undesirable microorganisms, such as bacteria, produce products such as acetic and lactic acids from glucose feedstocks, that not only consume the feedstock and thus prevent feedstock conversion to desired products, but also adversely affect desirable microorganisms in a biorefining process. For example, acetic and lactic acids adversely affect the rate at which *Saccharomyces cerevisiae* converts glucose to ethanol. The present invention utilizes SCD to control undesirable microorganisms, for example, during storage and transport, preserving the feedstock.

Carbohydrate feedstocks are a rich source of nutrients that can support the growth of various microorganisms. Carbohydrate feedstocks advantageously serve as both nutrients for a desirable microorganism, such as yeast in fermentation, and as starting materials for producing ethanol. However, undesirable microorganisms proliferate in the nutritional carbohydrate feedstock during storage and transportation prior to fermentation or other end use, resulting in deterioration of the feedstock. Moreover, undesirable microorganisms commonly associated with deterioration of carbohydrate feedstocks may naturally occur in any starting material for a biorefining process, or may be introduced from external sources such as process equipment, impurities in the feedstock itself, among others.

By "deterioration" of a carbohydrate feedstock is meant chemical conversion of a carbohydrate in the carbohydrate feedstock resulting from reaction of the carbohydrate with or consumption of the carbohydrate by the undesirable microorganism. For example, undesirable microorganisms may consume carbohydrates as a nutritional source for metabolism of the microorganisms for their proliferation. Alternatively, undesirable microorganisms can react with carbohydrates and convert the carbohydrate into a different chemical compound, without metabolizing the carbohydrate. For example, *Leuconostoc mesenteroides*, a bacterium that is naturally present in extracted sugarcane juice, converts sucrose, a disaccharide, into dextran, a polysaccharide. Conversion of sucrose to dextran results in lower yield when sugarcane juice is used to manufacture crystal sugar. Similarly, fermentation productivity is lower when sugarcane juice contaminated by *L. mesenteroides* is used in ethanol fermentation.

Stabilized Chlorine Dioxide

The term "stabilized chlorine dioxide" otherwise referred to herein as "SCD" means one or more chlorine dioxide-containing oxy-chlorine complexes, one or more chlorite-containing compounds, one or more other entities capable of forming chlorine dioxide when exposed to acid, and combinations thereof. Thus, stabilized chlorine dioxide comprises at least one of a chlorine dioxide-containing oxy-chlorine complex, a chlorite-containing compound, or an entity capable of forming chlorine dioxide in a liquid medium when exposed to acid. SCD is available commercially.

Among the preferred chlorine dioxide-containing oxy-chlorine complex is selected from the group consisting of a complex of chlorine dioxide with carbonate, a complex of chlorine dioxide with bicarbonate and mixtures thereof. Examples of chlorite-containing compounds include metal chlorites, and in particular alkali metal and alkaline earth metal chlorites. A specific example of a chlorite-containing compound that is useful as a chlorine dioxide precursor is sodium chlorite, which can be used as technical grade sodium chlorite.

SCD is preferably an aqueous solution of an alkali metal or alkaline earth metal chlorite, typically sodium chlorite ($NaClO_2$). Sodium chlorite in solution is generally stable at pH above 7, but releases the active chlorine dioxide ($ClO_2$), when the pH is lowered below neutral (pH 7). The rate of activation of SCD, that is, the rate at which the active $ClO_2$ is released from the stable form, increases as pH decreases.

The exact chemical composition of many of SCD compositions, and in particular, chlorine dioxide-containing oxy-chlorine complexes, is not completely understood. The manufacture or production of certain chlorine dioxide precursors is described by Gordon, U.S. Pat. No. 3,585,147 and Lovely, U.S. Pat. No. 3,591,515. Specific examples of commercially available and useful stabilized chlorine dioxide include, for example, ANTHIUM DIOXCIDE and FERMASURE, available from E. I. du Pont de Nemours and Company, Wilmington Del.; OXINE and PUROGENE, available from Bio-Cide International, Inc., Norman, Okla.

SCD may be provided as a solution of the one or more chlorine dioxide-containing oxy-chlorine complexes, one or more chlorite-containing compounds, one or more other entities capable of forming chlorine dioxide when exposed to acid, and combinations thereof. The solution provides SCD in a liquid medium at a predetermined concentration of actives as available chlorine dioxide (ClO$_2$). Preferably, the liquid medium has sufficient SCD to have an available chlorine dioxide concentration in the range of about 0.002% to about 40% by weight, preferably, in the range of about 2% to about 25% by weight, more preferably in the range of about 5% to about 15% by weight, based on the total weight of the liquid medium including the chlorine dioxide-containing oxy-chlorine complexes, chlorite-containing compounds, other entities capable of forming chlorine dioxide when exposed to acid, and combinations thereof.

SCD may be provided as a solid material, such as a composition comprising an alkali or alkaline earth metal chlorite powder, inert ingredients, and optionally dry activator such as a dry acid.

SCD may also be provided as a mixture (or slurry) comprising a saturated solution of alkali or alkaline earth metal chlorite powder and additional solid alkali or alkaline earth metal chlorite powder. Such slurries provide a liquid SCD with a higher active ingredient level than available in solution form.

The invention is hereinafter described in terms of SCD as stabilized alkali metal chlorite, more specifically sodium chlorite (NaClO$_2$). Typically sodium chlorite is used as an aqueous solution comprising 5-22% by weight, based on solution weight of sodium chlorite in water. Hereinafter SCD concentrations are described in terms of the concentration of chlorine dioxide available when the chlorite is stoichiometrically converted to chlorine dioxide, "available ClO$_2$". The content of potential chlorine dioxide in 1 g of sodium chlorite is 0.597 g. Sodium chlorite solutions comprising 5-22% by weight of sodium chlorite thus contain 2.98-13.13% available chlorine dioxide. The generation of ClO$_2$ is illustrated by the following equation (1):

$$5NaClO_2 + 4H^+ \rightarrow 4 ClO_2(g) + 2H_2O + Cl^- + 5Na^+ \tag{1}$$

wherein one NaClO$_2$ molecule provides 0.8 ClO$_2$ molecules.

The present invention comprises use of SCD as a preservative in carbohydrate feedstocks to suppress reaction of the carbohydrate with or consumption of the carbohydrate by microorganisms. Such contamination may occur at the source of production of the carbohydrate feedstock or during storage, transportation or other transfer prior to use of the feedstock. Carbohydrate feedstocks thus preserved maintain the carbohydrate content for use, such as in a biorefinery, or other consumption after storage and transport.

SCD is added to the carbohydrate solution in the range of 10 mg/kg to 10000 mg/kg as available chlorine dioxide, preferably in the range of 10 mg/kg to 5000 mg/kg, more preferably 50 mg/kg to 1000 mg/kg, and most preferably 100-500 mg/kg, as available chlorine dioxide. SCD is effective when the pH of the carbohydrate solution generally ranges between 2.6 and 9.

pH Limitations

SCD as defined herein comprises at least one of a chlorine dioxide-containing oxy-chlorine complex, a chlorite-containing compound, or an entity capable of forming chlorine dioxide in a liquid medium when exposed to acid. When SCD is an aqueous solution of sodium chlorite, the SCD has a pH of greater than pH 7. Sodium chlorite solutions release the active chlorine dioxide (ClO$_2$), as pH is lowered. The rate of chlorine dioxide release from SCD aqueous solutions increases as pH is reduced from pH of about 5 to 6 to 2.6. This rate may vary depending on several factors. For example, different ClO$_2$ precursors may release the ClO$_2$ at different rates within at the same or similar pH. Other factors such as the buffering capacity of a solution may affect the rate of ClO$_2$ release from SCD solutions. These factors are well known to those skilled in the art.

The pH of the feedstock is typically at least pH 2.6. The pH preferably ranges from a pH of 3 to pH 9, preferably 3.5 to 8, more preferably 4 to 7, and most preferably 4.5 to 7. If desired, pH may be raised by the addition of a base, such as an alkali or alkaline earth hydroxide or carbonate to the desired range. Similarly, if desired, pH may be lowered by the addition of an acid, such as citric, hydrochloric, or phosphoric, to the desired range. For example, the pH of corn mash is usually adjusted to between 4.5 and 5.8, to facilitate the efficacy of alpha-amylase and gluco-amylase enzymes, respectively.

The invention is hereinafter described in terms of SCD being a stabilized alkali metal chlorite, more specifically the most common and commercially available of the alkali metal chlorites, sodium chlorite (NaClO$_2$). By stabilized alkali metal chlorite is meant a buffered solution of the chlorite at a pH above 7, preferably pH of 9-10. The solution typically comprises 5-22% w/w sodium chlorite in water, although the concentration of sodium chlorite may also be higher or lower. Hereinafter SCD concentrations are described in terms of the concentration of chlorine dioxide available as ClO$_2$ when the chlorite is stoichiometrically converted to chlorine dioxide.

Process

The present invention is a process to preserve carbohydrate feedstocks comprising or consisting essentially of or consisting of contacting the carbohydrate feedstock with a stabilized chlorine dioxide ("SCD"). SCD includes alkali and alkaline earth metal chlorites. The stabilized chlorine dioxide comprises at least one of a chlorine dioxide-containing oxy-chlorine complex, a chlorite-containing compound, or an entity capable of forming chlorine dioxide in a liquid medium when exposed to acid. SCD is added in an amount to provide 10 to 10000 mg/kg of total available chlorine dioxide, based on total weight of the feedstock.

Preferably, SCD is added in an amount to provide 10 to 5000 mg/kg of total available chlorine dioxide, more preferably 50 mg/kg to 1000 mg/kg, and most preferably 100-500 mg/kg, as available chlorine dioxide.

In the process of the present invention, SCD is contacted with a carbohydrate feedstock, such as a mash, in an effective amount to protect the carbohydrate from the growth of undesirable microorganisms and thus to prevent deterioration of the feedstock. Deterioration of the feedstock can be determined by the populations of contaminant microorganisms present, or the concentration of microbial metabolites, such as organic acids, that generally indicate unintended and undesirable microbial activity in the feedstock. Microorganisms are thus substantially prevented from proliferating in the stored or transported feedstock following the addition of SCD.

Surprisingly, the carbohydrate feedstock treated according to this invention remains stable for at least one month. By "stable", it is meant herein the addition of SCD preserves the carbohydrate feedstock, where "preserve" is defined hereinabove as preventing reaction of or consumption of carbohydrate by contaminant microorganisms. A stable carbohydrate feedstock does not undergo an increase in the microbial population in the feedstock of more than 1 log$_{10}$ CFU/ml or 1 log$_{10}$ CFU/g. CFU, an abbreviation for colony forming unit, is a measure of microbial population in the feedstock. CFU is used to determine the number of viable microbial cells in a sample per unit volume or per unit mass, or the degree of microbial contamination in samples. A second measure of change is pH of the preserved feedstock should not change by more than 0.5 pH units. However, as previously stated, pH change may not be sufficient under all circumstances to monitor preservation of a carbohydrate feedstock.

The carbohydrate feedstock can be an aqueous solution or suspension comprising monosaccharides, disaccharides, oligosaccharides, polysaccharides, or mixtures thereof. The carbohydrate feedstock may comprise a fermentable sugar, in particular, when the feedstock is intended for use in production of sugar products (such as table sugar or molasses) for human consumption or for use in fuel ethanol fermentation. The carbohydrate feedstock may comprise up to 100% by weight of carbohydrates. Generally the carbohydrate feedstock comprises between 1% and 70% carbohydrate based on the total weight of the feedstock, preferably between 2 and 40%.

Surprisingly, the process is effective in the absence of added acid to generate chlorine dioxide. By the "absence of added acid" is meant herein that no acid is added or other method such as oxidation used to generate chlorine dioxide. The process is typically performed at a pH of at least 2.6. The pH preferably ranges from a pH of 3 to pH 9, preferably 3.5 to 8, more preferably 4 to 7, and most preferably 4.5 to 7.

In a second embodiment, SCD is contacted with a carbohydrate feedstock in a unit operation in which microorganisms have begun to deteriorate the feedstock. While loss of carbohydrate is irreversible, deterioration can be interrupted and the feedstock preserved for subsequent processing of the carbohydrates. In this embodiment, SCD is added in an amount to provide 50 to 10000 mg/kg of total available chlorine dioxide, based on total weight of the feedstock. Preferably, SCD is added in an amount to provide 100 to 5000 mg/kg, more preferably 100-1000 mg/kg, of total available chlorine dioxide.

Carbohydrate feedstocks preserved with SCD according to the process of this invention can be used in fermentation and other biorefinery processes. The SCD content, carbohydrate concentration, and pH may vary depending on specific desired processes parameters. These variations are well known to those skilled in the art.

In the present invention, SCD is used as a preservative for carbohydrate feedstocks to impede contaminant microorganism activity and subsequent deterioration of the carbohydrate feedstock. Contaminant microorganisms include bacteria as disclosed in WO 2007/149450 and contaminant yeast as disclosed in U.S. patent application Ser. No. 12/467,728, filed May 18, 2009. SCD inhibits growth of certain bacteria that cause undesired decomposition of carbohydrates such as simple sugars to deleterious acids and also selectively to reduce the activity of contaminant yeasts.

SCD can be used to control microbial spoilage of carbohydrate feedstocks such as sugar-based feedstocks and cellulose feedstocks. Cellulose feedstocks include unprocessed plant material such as switchgrass, or agricultural by-products such as corn stover and bagasse. Sugar-based feedstocks include sugarcane juice and molasses.

In certain biorefinery process, the pH of freshly processed sugarcane juice or molasses is approximately 5 (usually between pH 4.5 and pH 5.5). Sugarcane juice contains 10-15% sucrose, while molasses contains up to 50% sucrose. In this embodiment, SCD is contacted with the sugarcane juice or molasses. This contact may be immediately upon production, which is beneficial to impede microorganism activity if the product is intended for storage or transportation. Sugarcane juice and molasses tend to have naturally occurring high levels of contamination by microorganisms that contribute to sugarcane juice or molasses spoilage. Thus, contact with SCD according to this invention extends useful storage life of these products by reducing the capacity of spoilage microorganisms to grow in and deteriorate the juice or molasses. Depending on the pH and the sucrose (carbohydrate) concentration, a dose of 200-1500 mg/kg of SCD as available $ClO_2$ (e.g., 335-2510 mg/kg of sodium chlorite, based on total feedstock weight) is sufficient to prevent the growth of microorganisms in the cane juice or molasses.

Thus, in the process of this invention, there is improvement in storage and transportation of carbohydrate feedstock by reducing deterioration thus improving operation of downstream operations, such as fermentation.

EXAMPLES

The examples demonstrate the preservation of carbohydrates stored in the presence of SCD. In these Examples, SCD is a buffered solution of sodium chlorite (21% w/w) having a pH of 9.2, available from E. I. du Pont de Nemours and Company, Wilmington, Del.

Example 1

In this Example, SCD was used to control growth of spoilage bacteria in molasses. Molasses (available from B&G Foods, Inc., Roseland, N.J., carbohydrate content of about 50%) was diluted with 3.1 parts water to model industrial conditions. The diluted molasses solution was sterilized by autoclaving at a temperature of 121 ° C. The pH of the sterilized solution was 5.32. The solution was then divided into 7 individual 75-ml samples in individual 125-ml flasks. SCD was added to each flask to give a range of concentrations from 0 to 450 mg/kg, based on available $ClO_2$.

*Lactobacillus brevis* and *Lactobacillus plantarum*, bacteria known to contaminate industrial ethanol production, were used in this Example. The bacteria were separately grown overnight in deMan Rogosa and Sharpe (MRS) broth (available from Difco Laboratories, Inc., Sparks, Md.) at 32° C. The bacteria were then mixed together and inoculated into the individual samples to provide approximately $10^5$ bacteria/ml (as colony forming units/ml, expressed as "5 $\log_{10}$ CFU/ml").

Total viable bacteria in the samples herein was measured as a concentration of colony forming units (CFU) per unit of volume (i.e., CFU/ml) of sample. There is a direct correlation of concentration of bacteria in the samples and the CFU measurement. Thus, the higher the concentration of bacteria, the higher the CFU would be and vice versa. As a convention, CFUs are transformed mathematically into logarithmic values ($\log_{10}$CFU) to simplify comparisons between different treatments.

The ability of SCD to inhibit the growth of *L. brevis* and *L. plantarum* was measured by plating out samples from each flask. At 24-hour (h) intervals, samples were withdrawn from each flask, diluted using sterile phosphate-buffered saline (available from Sigma-Aldrich, Inc., St. Louis, Mo.) and plated (0.1 ml) onto the surface of MRS plates. Plates were incubated at 32° C. and resultant colonies were counted, the results are shown in Table 1.

TABLE 1

Response of *L. brevis* and *L. plantarum* to treatment with stabilized chlorine dioxide at 32° C. in diluted molasses

| SCD concentration | $\log_{10}$ CFU/ml | | |
|---|---|---|---|
| | 0 h | 24 h | 48 h |
| 0 mg/kg | 5.0 | 8.53 | 9.3 |
| 37.5 mg/kg | 5.0 | 8.79 | 8.88 |

TABLE 1-continued

Response of *L. brevis* and *L. plantarum* to treatment with stabilized chlorine dioxide at 32° C. in diluted molasses

| | $Log_{10}$ CFU/ml | | |
|---|---|---|---|
| SCD concentration | 0 h | 24 h | 48 h |
| 75 mg/kg | 5.0 | 2.27 | 3.38 |
| 112.5 mg/kg | 5.0 | <1 | <1 |
| 150 mg/kg | 5.0 | <1 | <1 |
| 300 mg/kg | 5.0 | <1 | <1 |
| 450 mg/kg | 5.0 | <1 | <1 |

Table 1 shows the initial bacterial concentration in all of the samples was 5.0 $log_{10}$ CFU/ml of molasses as inoculated and analogous to what might be seen at industrial scale. The control sample that received no SCD treatment allowed the bacteria to grow from 5.0 $log_{10}$ CFU/ml to 8.53 $log_{10}$ CFU/ml in 24 h and to 9.3 $log_{10}$ CFU/ml after 48 h, both at 32° C. Treatment with 37.5 mg/kg SCD limited growth to 8.88 $log_{10}$ CFU/ml after 48 h. Treatment with 75 mg/kg SCD reduced the concentration of bacteria in the sample from 5.0 to 2.26 $log_{10}$ CFU/ml after 24 h and to 3.38 $log_{10}$ CFU/ml after 48 h. At all SCD concentrations higher than 100 mg/kg tested, the number of *L. brevis* and *L. plantarum* that could be recovered from the molasses samples was below the detectable limit. Table 1 indicates that treatment with SCD at these concentrations is able to inhibit the growth of bacteria and therefore reduce the bacterial deterioration of molasses intended for use as a feedstock.

Example 2

The rate of chlorine dioxide release (generation) from SCD was determined by activation using lactic acid, a common acid produced by contaminant bacteria found in carbohydrate feedstocks. In this example a 250 mg/L SCD solution was acidified with lactic acid to generate $ClO_2$ at ambient temperature. An approximate 250 mg/L SCD solution was made by diluting a stock FermaSure® XL solution with water. Portions of the 250 mg/L SCD solution were then acidified to pH between 2.2 and 3.2 using a dilute, <2%, lactic acid solution. An Accumet pH Meter 25 (available from Fischer Scientific Company, Fair Lawn, N.J.) was used to monitor the solution pH of the solution. The acidified 250 mg/L solution was then analyzed for $ClO_2$ concentration using a HACH DR/2000 spectrophotometer (available from Hach Company, Loveland, Colo.), which was calibrated at 400 nm, 420 nm and 445 nm for $ClO_2$. Data from the spectrophotometer was collected at 10 second intervals, using a DELL computer and HACH Link 2000 data logging software, for up to 24 hours. A summary of $ClO_2$ generation data is in Table 2.

TABLE 2

Rate of release of $ClO_2$ versus time

| | $ClO_2$ Formed After Time (mg/kg) | | | | | | |
|---|---|---|---|---|---|---|---|
| pH | 1 h | 4 h | 8 h | 12 h | 16 h | 20 h | 24 h |
| 2.2 | 21 | 47 | 63 | 78 | 89 | 98 | 105 |
| 2.4 | 8 | 25 | 40 | 52 | 61 | 69 | 72 |
| 2.6 | 5 | 14 | 23 | 32 | 39 | 44 | 48 |
| 2.8 | 3 | 9 | 15 | 20 | 25 | 29 | 32 |
| 3.0 | 2 | 7 | 12 | 17 | 20 | 22 | 25 |
| 3.2 | 1 | 4 | 7 | 9 | 12 | 12 | ND* |

*Not determined.

Table 2 shows release of chlorine dioxide from SCD is relatively slow, even at low pH. Thus, when SCD is contacted with a carbohydrate feedstock at pH of at least 2.6, without adding acid, it is surprising that the SCD has a preservative effect. That is, growth of bacteria, which occurs through consumption of carbohydrate, is substantially prevented, when concentration of $ClO_2$ is expected to be very low.

What is claimed is:

1. A process to preserve a carbohydrate feedstock against microorganisms comprising contacting a carbohydrate feedstock in a unit operation wherein a unit operation is storage or transport with a stabilized chlorine dioxide at a pH of at least 2.6 in the absence of added acid to generate chlorine dioxide for a period of time of at least one month prior to use of the feedstock in a fermentation process, wherein the concentration of the carbohydrate is at least 1%, by weight of the feedstock, and the amount of stabilized chlorine dioxide added is 10 to 10000 mg/kg as $ClO_2$, based on total feedstock weight, wherein microbial population in the feedstock does not increase more than 1 $log_{10}$ CFU/ml or 1 $log_{10}$ CFU/g over a period of time of at least one month.

2. The process of claim 1 wherein the concentration of carbohydrate in the feedstock is 1.0 to 70%, based on the total feedstock weight, and the pH is at least 3.

3. The process of claim 1 wherein the carbohydrate is a naturally-occurring carbohydrate, having a reducing end group.

4. The process of claim 3 wherein the carbohydrate is a monosaccharide, disaccharide, oligosaccharide, polysaccharide, or mixtures of two or more thereof.

5. The process of claim 1 wherein the carbohydrate feedstock is a solution or suspension of a fermentable sugar.

6. The process of claim 5 wherein the carbohydrate feedstock is corn steep liquor.

7. The process of claim 1 wherein the carbohydrate feedstock is molasses.

8. The process of claim 1 wherein the carbohydrate feedstock further comprises enzymes, surfactants, dispersants, antifoaming compositions, minerals, trace elements, and combinations of two or more thereof.

9. The process of claim 1 wherein the carbohydrate feedstock is a cellulose feedstock.

10. The process of claim 1 wherein the stabilized chlorine dioxide is one or more chlorine dioxide-containing oxy-chlorine complexes.

11. The process of claim 1 wherein the stabilized chlorine dioxide is one or more chlorite-containing compounds.

12. The process of claim 10 wherein the one or more chlorine dioxide-containing oxy-chlorine complexes is a complex of chlorine dioxide with carbonate, a complex of chlorine dioxide with bicarbonate or a mixture thereof.

13. The process of claim 11 wherein the one or more chlorite-containing compounds is an aqueous solution of an alkali metal or alkaline earth metal chlorite.

14. The process of claim 13 wherein the one or more chlorite-containing compounds is an aqueous solution of an alkali metal chlorite.

15. The process of claim 14 wherein the alkali metal chlorite is sodium chlorite.

16. The process of claim 11 wherein the pH is 3 to 9.

17. The process of claim 11 wherein the pH is 3.5 to 8.

18. The process of claim 11 wherein the pH is 4 to 7.

19. The process of claim 11 wherein the pH is 4.5 to 7.

* * * * *